United States Patent [19]

Deysarkar et al.

[11] Patent Number: 4,959,995
[45] Date of Patent: Oct. 2, 1990

[54] AUTOMATED COLD CRANK SIMULATOR

[75] Inventors: Asoke K. Deysarkar, Katy; Ralph J. McCloskey, Conroe, both of Tex.

[73] Assignee: Pennzoil Products Company, Houston, Tex.

[21] Appl. No.: 298,257

[22] Filed: Jan. 17, 1989

Related U.S. Application Data

[63] Continuation of Ser. No. 8,663, Jan. 30, 1987, abandoned.

[51] Int. Cl.$^5$ .............................................. G01N 11/00
[52] U.S. Cl. .......................................... 73/54; 137/92
[58] Field of Search ................... 73/54, 56, 55, 57, 59, 73/60; 137/92, 4

[56] References Cited

U.S. PATENT DOCUMENTS

| | | | |
|---|---|---|---|
| 2,955,459 | 10/1960 | Cihelka et al. | 73/57 |
| 2,988,914 | 6/1961 | Jones | 73/54 |
| 3,074,266 | 1/1963 | Sadler et al. | 73/55 |
| 3,234,781 | 2/1966 | Bragg | 73/55 |
| 3,559,463 | 2/1971 | Tovrog et al. | 73/55 |
| 3,895,513 | 7/1975 | Richardson | 73/55 |
| 4,027,516 | 6/1977 | Ochodnicky et al. | 73/57 |
| 4,048,056 | 9/1977 | Romovacek | 73/57 |
| 4,472,963 | 9/1984 | Gyer et al. | 73/60 |
| 4,544,489 | 10/1985 | Campbell et al. | 137/92 |

FOREIGN PATENT DOCUMENTS

| | | | |
|---|---|---|---|
| 635340 | 11/1983 | Belgium | 73/57 |
| 2531538 | 6/1984 | France . | |
| 899369 | 6/1962 | United Kingdom | 73/57 |

*Primary Examiner*—Hezron E. Williams
*Attorney, Agent, or Firm*—Lowe, Price, Leblanc, Becker & Shur

[57] ABSTRACT

Apparatus for unattended retrieval of samples of material to be tested for viscosity provides substantially continuous monitoring capability for a blending plant. A single device is used for both retrieving the samples from a pipe conveying the material and for delivering the samples to a measuring chamber of a viscometer. The device, such as a pump or a solenoid operated valve, is controlled by a sequence timer programmed to generate a timed sequence of signals. Preferably, the device is operated to provide a new sample to the viscometer when the measuring chamber is being heated, thereby displacing the previous sample without requiring a cleansing agent.

12 Claims, 5 Drawing Sheets

AUTOMATED COLD CRANK SIMULATOR

This application is a continuation of application Ser. No. 008,663, filed Jan. 30, 1987, now abandoned.

TECHNICAL FIELD

This invention relates to viscometers, and more particularly to automated viscometers for continuous monitoring of a product of a bottling or canning plant, and still more specifically to cold cranking simulators for continuously monitoring viscosity of automotive petroleum products.

BACKGROUND ART

Viscometers, which are devices for measuring viscosity of materials, operate according to known principles and standards. One such viscometer is described in Cannon et al Pat. No. 3,277,694, assigned to the Cannon Instrument Company of State College, Penna.

Of particular interest to the present invention is a commercially available viscometer, a cold cranking simulator provided under the designation CCS by the Cannon Instrument Co. Such a viscometer is used in the petroleum industry for measurement of oil viscosity in accordance with a standardized test procedure D2602 established by the American Society for Testing and Materials (ASTM).

In a typical application, oil samples are provided to a measurement station using a viscometer such as the CCS, where appropriate measurements are conducted under the established standards, to determine a proper viscosity grading for the petroleum product. The measurement procedure requires manual injection of the sample to a sample chamber, passing of appropriate temperature fluids in the vicinity of the sample for temperature control of the sample, and measurement of the sample viscosity at the appropriate temperature. Cleansing of the measurement chamber between samples is required in order to avoid contamination of successive samples, and separate cleansing fluids are used for that purpose.

However, the above described prior art procedure is labor intensive and thus expensive. Further, because of manual supply of the samples to the viscometer, an opportunity exists for errors to occur. Particularly, an operator may provide the wrong sample for measurement, or provide a single grade base stock for a multi-grade product, so that mislabeling of the product may thus result.

Moreover, for a system using a cleansing solution of the measurement chamber there must be provided adequate disposal of the solvent. Thus an environmental problem is caused by such a device.

Additionally, manual operation of the viscometer is time consumptive and may require several attempts to complete a single measurement.

In order to overcome some of the above described difficulties, it has been proposed to provide an automated cold cranking simulator, requiring a reduced amount of manual intervention. In such a prior art simulator, a microprocessor controlled programmable current source has been used to minimize operator intervention. Similarly, a microprocessor has been used to maintain appropriate temperatures for the coolant fluids for both hot and cold baths of the simulator.

While such a prior art cold cranking simulator overcomes some of the difficulties of the prior art, a problem of still greater significance remains without solution.

A significant difficulty of the prior art is the fact that continuous, unattended and automated monitoring of a product of a blending plant has heretofore been impossible. Even in the improved viscosity measurement devices, manual loading is required of a sample changer carouse. An operator is required to load syringes with both test samples and reference samples. Thus, after conducting the measurements the syringes used in the sample delivering carousel must either be cleaned or discarded. Moreover a rotatable magazine, or carousel, as used in the prior art to provide a plurality of syringes to the viscometer, is susceptible to jamming.

Accordingly, it is seen that continuous, unattended monitoring is not provided even by he improved prior art system. Moreover, operator error may still occur in providing the wrong samples for measurement, or in providing the wrong reference sample for comparison. Additionally, a further processing step is required to cleanse the syringes after the measurement, adding to the expense of operation of the device. Aternatively, if the syringes are discarded subsequent to measurement, still another expense must be incurred by the more recent systems.

Since cold cranking simulator viscosity is a primary indicator used for maintenance of quality control during bending of multigrade motor oils, repeated, unattended monitoring of this parameter, i.e., continuous nonitoring would provide a significant improvement of product quality assurance. The failure of the prior art to provide a continuous monitoring process for cold cranking viscosity thus adds to the degree of uncertainty in product viscosity and product reliability and to a decrease in quality control.

In a typical bending plant, CCS viscosity measurements are performed from ten to fifteen times per day to insure product quality. Thus much of the blended product is provided without viscosity data. However, in view of the labor intensive approaches of the prior art it has thus far been too difficult or expensive to increase the number of viscosity measurements.

As is known in the art, a viscosity improver (VI) is added to multi-grade motor oils in response to the viscosity measurements, thus providing an optimal formulation of multi-grade oils. However, since the polymers in a VI improver form deposits on engine parts and may adversely affect engine operation, it is desirable to add a minimum quantity of the VI to the oils and yet to add a sufficient quantity to attain the desired viscosity.

In order to achieve and maintain the desired balance, wherein enough VI is added to provide the required viscosity while holding engine deposits to a minimum, it is necessary for the bender to have continuous feedback of CCS viscosity data during blending.

Continuous monitoring of viscosity data is also quite helpful in avoidance of the wrong base stock in the bending process, such as use of Bright Stock instead of 100N for production of 5W-30 motor oil. Under a continuously monitored bending operation, provision of the wrong stock quickly results in viscosity readings which deviate from the expected values, thus alerting the blender to a quick correction of the error. There is accordingly a need in the prior art for automated, unattended and substantially continuous monitoring of CCS data for a bending process. Without such continuous, unattended, monitoring it is impossible to provide full automation of a blending, bottling or canning facility.

DISCLOSURE OF INVENTION

It is accordingly an object of the invention to overcome he difficulties of the prior art and to provide unattended, substantially continuous, monitoring of a cold-temperature viscosity measuring apparatus.

It is a more specific object of the invention to provide autonomous viscosity monitoring of a blending facility by providing a single means for extracting a sample and for delivering the sample to a viscometer.

Yet another object of the invention is the provision of a computer control for a viscometer, for automated cold cranking simulation wherein microprocessor is programmed to generate a sequence of signals in order to cause a sequence of operations to be performed substantially unattended in connection with a viscosity measurement.

It is still a further object of the invention to provide an automated viscosity measurement apparatus wherein a programmed microprocessor is operable for determining a heating operation in a measuring chamber of the viscometer and, responsive thereto, said microprocessor is further operable for causing a single means to withdraw a sample from a line and to introduce the sample to the measuring chamber, thereby to displace the previous sample and to eliminate a need for a cleansing agent between successive samples.

It is yet a further object of the invention to provide a solenoid controlled valve or pump between a product delivery line and a measuring chamber of a viscometer for performing both the function of withdrawing a sample from the line for viscosity measurement and the function of introducing the sample into the measuring chamber, thus eliminating a need for manual handling of the sample.

Still another object is the provision of a pressure regulator between a pressurized product delivery line and a solenoid controlled valve for providing a sample to the solenoid controlled valve at a substantially regulated pressure for delivery to the measuring chamber of a viscometer.

In accordance with these and other objects of the invention, there is provided an improved viscosity measurement apparatus which includes a conveying means for conveying samples from a product delivery line to a measuring chamber of a viscometer and a timing means for automatically controlling the conveying means to provide repeated unattended end substantially continuous delivery of samples to the measurement chamber Additionally, there is provided a heat exchanger in the viscometer, including a bath and a heater for a heat exchange liquid, and a valve for controlling provision of the liquid to heat exchange with the measuring chamber. The timing means is operable for controlling both the heat exchange valve and the conveying means for the sample.

Moreover, in order to eliminate a cleansing operation between samples, the timing means may be operable for causing the conveying means to convey the sample when the chamber is being heated, thus using one sample to displace another.

In accordance with one aspect of the invention, the conveying means may comprise a controllable pump between the product delivery line and the measuring chamber, under control of the timing means. Alternatively, a solenoid controlled valve may be used, similarly under control of the timing means.

A sample pump may be provided for situations wherein the pressure in the product delivery line falls below a threshold value therefor, and/or a pressure regulator may be provided for situations wherein the pressure in the line rises above an upper threshold value therefor.

In accordance with a further aspect of the invention, there is preferably provided an output device, such as a printer, chart recorder, and/or alarms which may be provided along with a display, for providing a record of the substantially continuous viscosity measurements for the product.

In accordance with the invention, the conveying means is a single means for both retrieving the samples from the product to be measured and for supplying the samples to the measuring chamber.

The foregoing and other objects, features and advantages of the present invention will become more readily apparent to those skilled in the art to which the invention pertains upon reference to the following detailed description of one of the best modes for carrying out the invention, provided by way of illustration and not of imitation of the invention, particularly when considered in conjunction with the accompanying drawing in which a preferred embodiment of the invention is shown.

BRIEF DESCRIPTION OF THE DRAWINGS

In accordance with the disclosure of the invention, the accompanying drawing is provided to illustrate the invention, wherein:

FIG. 6, comprising

BEST MODE FOR CARRYING OUT THE INVENTION

Figure 1:
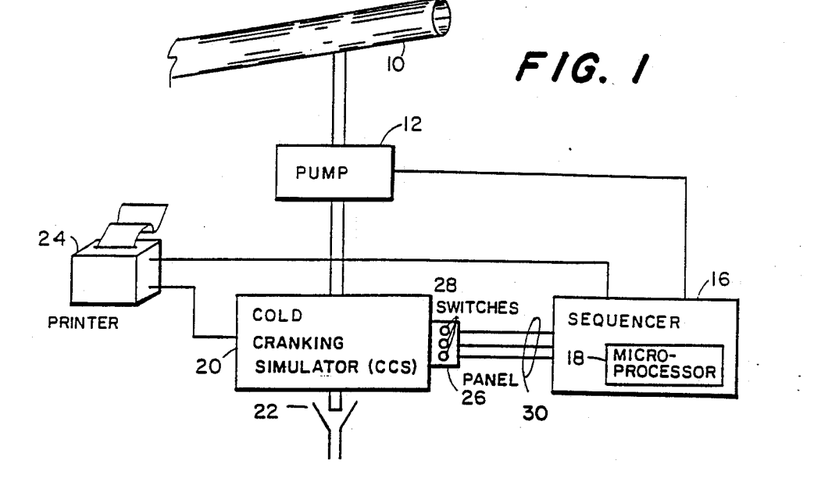
FIG. 1 shows a block diagram representation of one embodiment of the present invention.

Referring now to FIG. 1, there is shown a representation of an improved viscosity measuring system wherein cold cranking data is obtained for petroleum products. Although the present invention contemplates application of the inventive concept to obtaining viscosity data for blended singe grade or multigrade oils, it should be recognized that the concepts of the invention may be applied to other measurement devices, for other products.

Figure 2:
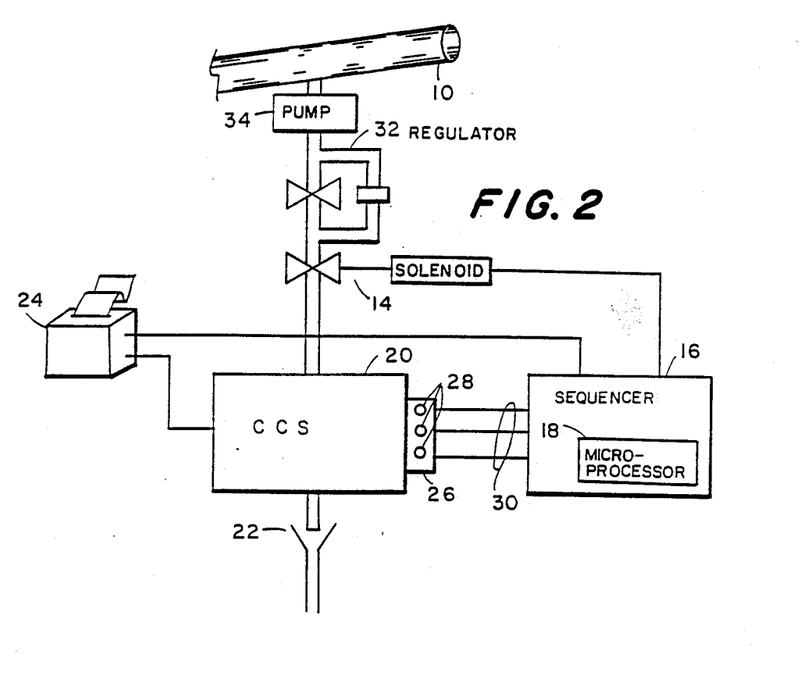
FIG. 2 shows a block diagram representation of a second embodiment of the invention.

As shown in FIG. 1, the material to be measured, which may be motor oils, for example, is provided in a pipeline 10, conveying the product to a bottling or canning device therefor. The pipeline 10 may or may not be pressurized. For a pipeline conveying the product in a low-pressurized state, or in an unpressurized state, a positive displacement, controllable pump 12 is provided, as shown in FIG. 1. For pressurized pipelines, a solenoid controlled valve assembly 14, shown in FIG. 2, is preferred In both embodiments, a sequencer 16, generating a number of sequentially timed control signals, is provided. The sequencer may be operated under control of a microprocessor 18.

A viscometer is provided in a cold cranking simulator 20 for obtaining viscosity measurements of the product in pipeline 10 under varying temperature conditions. The cold cranking simulator 20 is arranged to receive a quantity of the material to be measured from pump 12, or from the solenoid valve assembly 14. The structure and operation of the cold cranking simulator 20 are known in the art, and will not be repeated herein. As may be seen upon reference to FIGS. 1 and 2, cold cranking simulator 20 discharges the tested material through a chute assembly 22.

In accordance with the present invention, the results of the measurement are provided to B user via a printer 24, or another output or device. Preferably, printer 24 provides a written record of viscosity measurements, batch identification numbers, motor current for cold cranking simulator 20, temperature and other identifying data. Any recording device may be used, and a display such as a CRT terminal (not shown) or the like may also be provided.

In typical operation, the cod cranking simulator 20 receives a sample of the material to be measured. A panel 26 having a plurality of function selecting and controlling switches 28 is provided thereon. In accordance with the invention, the functions of switches 28 are performed by control signals generated by sequencer 16, provided via connecting lines 30. Thus, the appropriate functions of the simulator 20 are performed in sequences determined by the microprocessor 18.

As is also seen in the embodiment of FIG. 2, a pressure regulator 32 is provided between the pipeline 10 and the valve assembly 14. Thus for situations in which the pipeline pressure exceeds a predetermined threshold, regulator 32 will reduce the pressure to an acceptable range, so that the product sample may be directly provided to a measuring chamber of the cold cranking simulator 20. Still further, in a situation wherein the pressure in pipeline 10 falls to a value below a further threshold, and is insufficient to convey the product through the valve of solenoid valve assembly 14, an auxiliary pump 34 is provided. Auxiliary pump 34 is activated by sequencer 16 to provide a sample to cold cranking simulator 20 similary to activation of pump 12 in FIG. 1. However, pump 34 is used in a backup capacity for solenoid valve assembly 14.

Figure 3:
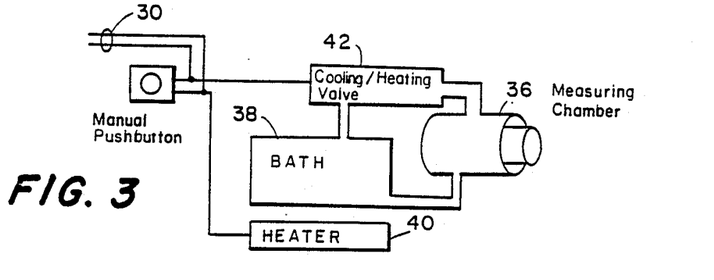
FIG. 3 shows a symbolic arrangement of the cold cranking simulator of FIGS. 1-2, modified to accept control signals in accordance with the invention.

Referring now to FIG. 3, a portion of the cold cranking simulator 20 is shown to illustrate operation of the device. Particularly, manual pushbuttons 28 may be used to activate the heating/cooling system of the cod cranking simulator to bring the product sample to the appropriate temperature for performing the viscosity test. Within simulator 20 there is provided a measuring chamber for conducting the test, shown symbolically at 36. Heating fluids are kept at predetermined temperatures in a bath 38 by a heater 40. A valve 42 is controlled to provide cooling or heating fluids to the measuring chamber 36, thus to heat or cool the sample, as appropriate.

While the prior art required manual actuation of pushbuttons 28, the present invention provides control signals on lines 30 to the internal wiring of cod cranking simulator 20. Thus, once a sample has been supplied to the simulator, the remaining operations are carried out under control of sequencer 16. Inasmuch as the sample is also provided to simulator 20 under control of the sequencer in response to control signals provided to a single device for withdrawing the sample from line 10 and for supplying the same to chamber 36, it is seen that the present invention permits substantially unattended, autonomous, and continuous measurement of viscosity parameters to be performed.

It should be appreciated that while a single device is preferred for performing both the functions of withdrawing the sample and providing the sample to the simulator, more than one device may be used. The advantages of the present invention will accrue as long as each of the devices is controlled by the sequencer 16.

Figure 4:
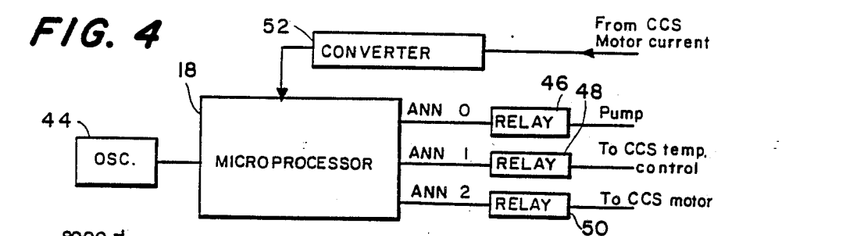
FIG. 4 shows a connection arrangement for the microprocessor of FIGS. 1-2 to carry out the invention.

Referring now to FIG. 4, a connection arrangement is shown for microprocessor 18 wherein various output signals are generated thereby and several input signals are provided thereto. More specifically, as will be appreciated from the description associated with the flow chart of FIG. 6, comprising FIGS. 6A and 6B, microprocessor 18 generates control signals for pump 12, for heater 40 and cooling/heating valve 42, and for the motor of cold cranking simulator 20. Additionally, microprocessor 18 monitors the current of the simulator motor, and counts the number of pulses generated by an oscillator 44 to keep track of the time of day and elapsed time during operation.

As shown in the Figure, microprocessor 18 generates three output signals, via annunciator ports 0, 1 and 2. The three signals are respectively used to activate pump 12, temperature control devices 40 and 42, and a motor of the cold cranking simulator 20. Thus, each of tho signals is provided to an appropriate one of a plurality of relays 46, 48 and 50, for activating the respective devices.

A converter 52 is used to provide motor current data to the microprocessor 18 controlling sequencer 16. Preferably, converter 52 is in the form of a signal amplifier, a sawtooth wave generator, and a voltage comparator connected o a paddle input of the sequence controlling microprocessor 18. When the paddle input is sampled, the wave generator is triggered to generate a waveform which drops linearly from 5 volts to 1 volt in three milliseconds. This voltage is continuously compared with the amplified input signal. When the voltage signals are equal, he paddle input signal is shunted to ground. This circuit serves to accurately convert simulator motor current to a decay time which can be read by the paddle timer circuit of computers.

Alternatively, the amplified simulator motor current can be used to bias a linear transistor circuit which is connected to the paddle input of the microprocessor. The decay time of this circuit can be read by the paddle timer.

As yet another alternative, in sequencers without analog input and storage capabilities the amplified simulator motor current may be connected to a sample-and-hold circuit, such that at the time when the simulator moor current is sampled, a contact is closed, causing the sample-and-hold circuit to read the input and update its memory. The output of the sample-and-hold circuit is a continuous analog output of the memory contents. The output of the sample-and-hold circuit is connected to display, recording, and alarm equipment.

Figure 5:
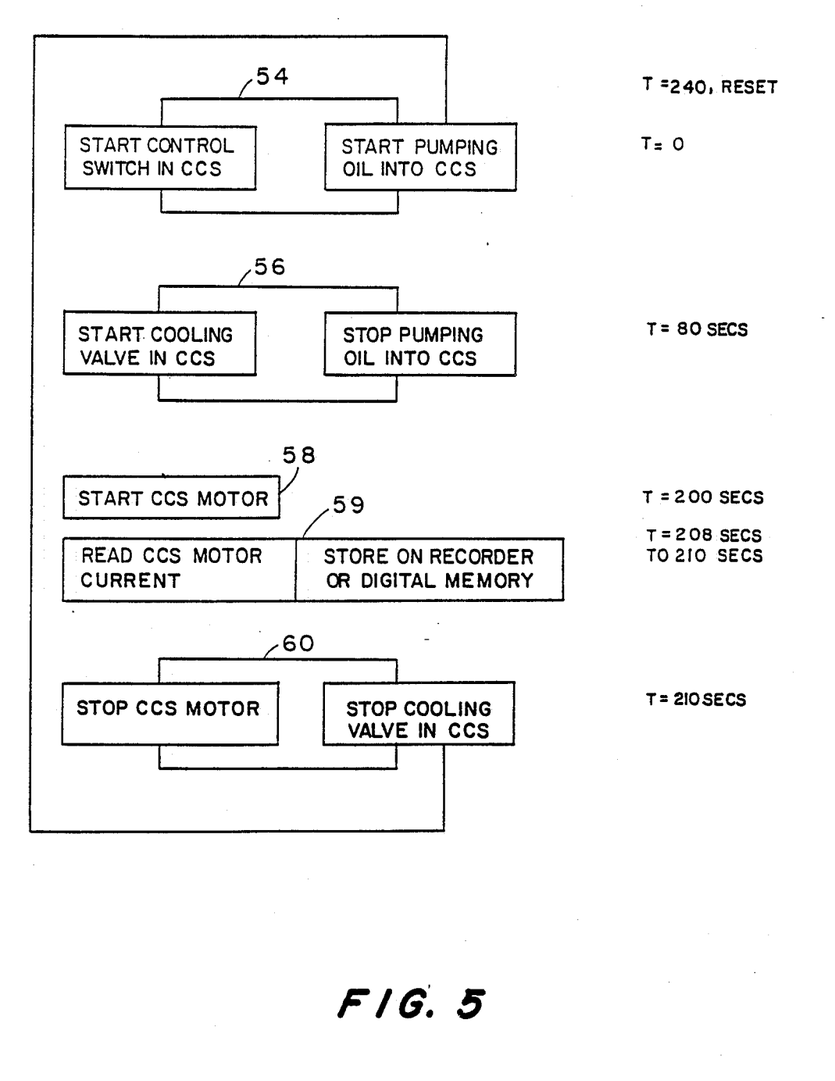
FIG. 5 shows a sequence of operations performed by the sequencer of FIGS. 1 and 2.

Referring now to FIG. 5, there is shown a broad description of the sequence of operations carried out by the inventive arrangement, and particularly by the microprocessor controlled sequencer As shown in the Figure, upon initiation of operation there is provided a sequence of steps wherein the pump 12, or solenoid valve 14, is activated by a signal from relay 46. For simplicity of disclosure, he following description refers to pump 12. However it should be understood that the description is equally applicable to the embodiment of FIG. 2, wherein solenoid valve 14 is used.

As will become apparent from the following description, particularly of the detailed flow chart of FIG. 6, prior to activation of cold cranking simulator 20 by sequence 54, the heater thereof is first activated to warm the measuring chamber 36 and any residue of a previous sample therein.

Thus, at sequence 54, after activating the heater, a control switch of the cod cranking simulator 20 is started and pump 12 is activated to start pumping the product, i.e., a particular motor oil blend, from pipeline 10 to the simulator. Thereafter, a sequence of steps is performed, as illustrated at 56, for causing the heating to stop or, equivalently, for causing cooling to start) and for reactivating pump 12. Sequence 58 refers to a number of steps used to start the simulator motor, while sequence 59 provides a reading of the CCS motor current and storage of the appropriate value on a recorder or in a digital memory. Sequence 60 refers to a number of steps which are executed by the microprocessor 18 to stop the simulator motor and to terminate cooling or, equivalently, to initiate heating prior to providing the next sample in sequence 54.

Prior to describing the details of the program used to control microprocessor 18, reference is once again made to the connection of FIG. 4. Therein, oscillator 44 is shown as providing an input to the microprocessor, the input being poked to a predetermined memory location. During execution of the program, the memory location is accessed to determine whether an oscillator signal has been received Receipt of the oscillator signal is used in timekeeping operations, by incrementing a counter, and for maintaining an up to date time of day. Oscillator 44 is preferably a 4 Hertz timer crystal which cycles from 0.5 volts to 0 volts.

In the program, various specific memory locations are used to retain values used in providing control signals for activating relays 46, 48 and 50. Thus, by poking the specific locations, microprocessor 18 causes sequencer 16 to turn pump 12 ON or to turn the pump OFF. By poking other locations, microprocessor 18 causes the sequencer to turn the heater ON or OFF, while still other memory locations are poked to turn the simulator motor ON or OFF.

Figure 6A:
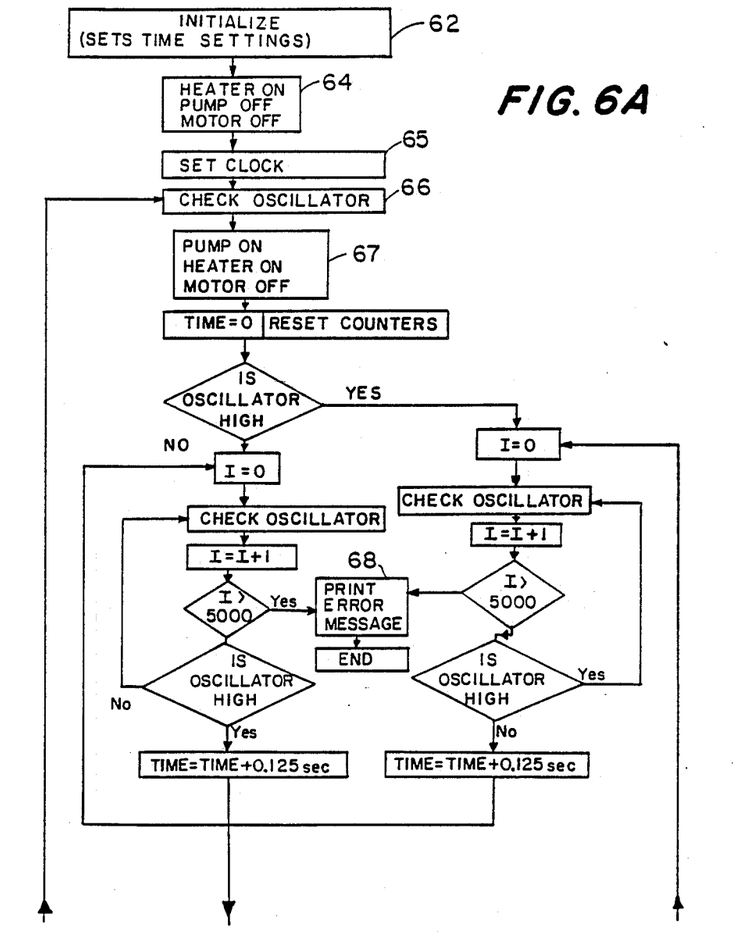
FIGS. 6A and 6B, shows a detailed flow chart for a program executed by the controller for the sequencer of FIGS. 1 and 2.
Figure 6B:
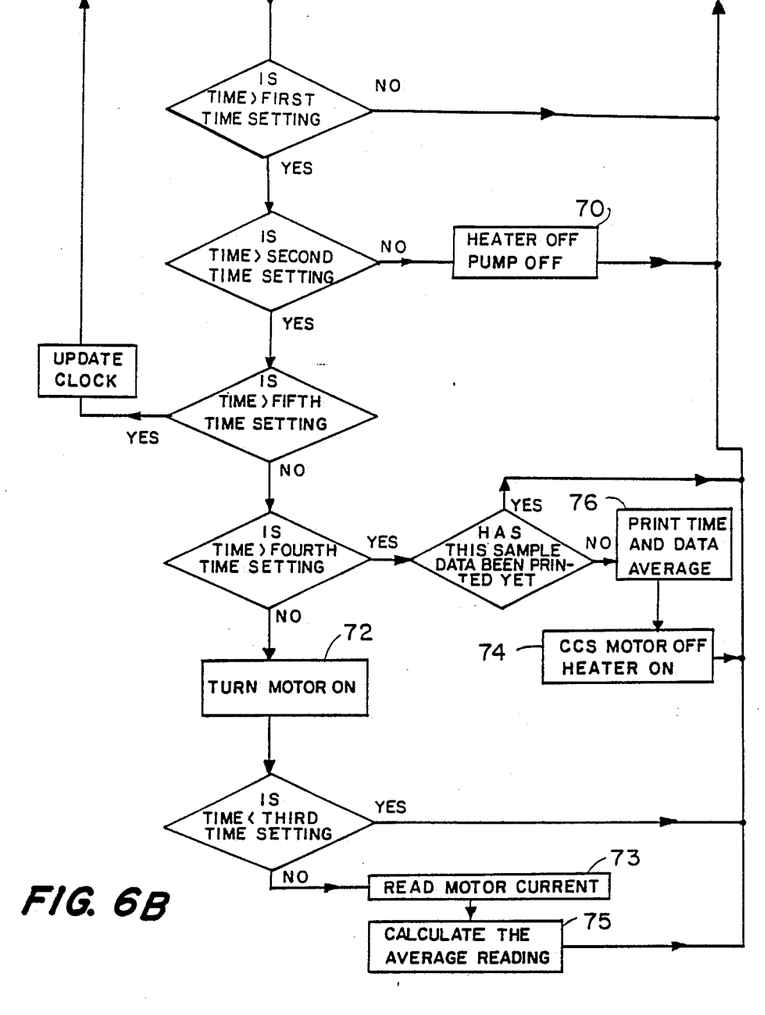

The program used to control microprocessor 18 to perform the sequence of FIG. 5 is provided in Appendix A hereof. A flow chart therefor is illustrated in FIG. 6A and 6B.

Briefly, it is seen in the flow chart that after initialization at step 62 the microprocessor 18 causes sequencer 16 to generate signals for turning ON the simulator heater and for turning OFF the pump 12 and the simulator motor. Thereafter, the clock is set and the oscillator count determined at steps 65 and 66. With the heater ON and he motor OFF, at step 67 the pump is turned ON. Consequently, the sample is provided to a heated, or warmed, measuring chamber.

An advantage of such a sequence is that a process step of test procedure D2602 is eliminated. The procedure specifically calls for injection of two solvents (acetone and hexane) into the measuring chamber to clean the cell thoroughly between samples. However, by heating the chamber at step 64 prior to introduction of the new sample, the new sample is provided as a cold, high viscosity fluid while the old sample is a warm, low viscosity fluid.

Thus, the new sample is used to provide a piston-like displacement of the old sample, eliminating the necessity for the additional process step. Preferably, he heating step 64 is used to heat the measuring chamber to a temperature of 35° C. and thus to warm the previous sample and reducing the viscosity thereof, permitting the new sample at a higher viscosity to displace the same.

Various timing steps are carried out by the program of flow chart 6, and if too much time is detected to have passed, at step 68 microprocessor 18 causes printer 24 to print an error message.

At step 70 the microprocessor causes generation of signals which start operation of cooling valve 42 in the simulator and which turn off pump 12, as previously described with respect to sequence 56 of FIG. 5. At step 72 the simulator motor is turned ON, as described with respect to sequence 58, while at step 74 the motor is turned OFF and the heater is turned ON, in accordance with sequence 60 of FIG. 5. At steps 73, 75 and 76 the value of the monitored motor current is read, its average calculated, and the time and average are printed, in accordance with sequence 59 of FIG. 5.

Thus, in accordance with the present invention, a cold cranking simulator is automated to perform substantially unattended withdrawal and delivery of samples for testing, measuring and reporting of viscosity values for motor oil blends.

To confirm that the inventive arrangement operates in conformity with the procedures of D2602, and that an oil blend provides substantially identical results for both the standard approach and that hereinabove described, a number of experiments were performed wherein various oils were tested at various temperatures, and at various sequences. As is apparent from the following summary of experimental results, the present invention provides substantially identical viscosity measurements as provided by a standard, non-automated, simulator operating in accordance with procedure D2602.

From the ASTM D-2602 procedure the sequence of steps shown in FIGS. 5 and 6 were run using the automated CCS. The results of the experiments, summarized in Tables 1-4, are provided in Appendix B.

Seven reference oils were tested at four different temperatures. The CCS viscosity data from these tests are tabulated in Table 1. For the same seven oils, CCS viscosity data using ASTM D-2602 are presented in Table 2.

In Table 1, it should be noted that in gathering CCS viscosity data for the reference oils, every possible sequence of pumping was used. For example, at −10° C., after CCS viscosity was measured for CL 32 reference oil, it was pumped out by CL 38, which is a higher viscosity oil than CL 32. The data in Table 1 indicates that after two measurements the CCS viscosity of CL 38 was the same as the one measured by ASTM D-2602. Again at −10° C., a lower viscosity oil (CL 32) was pumped after data was gathered for a higher viscosity liquid (CL 60). As seen from the two tables, the automated viscosity measurement stabilizes to ASTM value after two successive pumpings.

Figure 7:
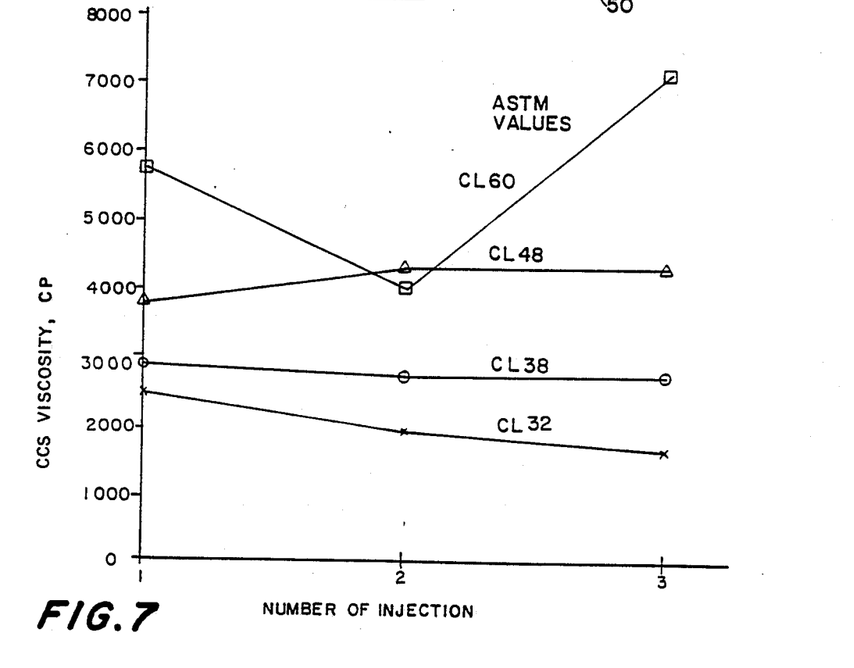
FIG. 7 shows a graphical representation of experimental results achieved with the present invention.

A comparison of the CCS viscosity data for all seven reference oils using ASTM procedure D-2602 (Table 2) and the inventive automated method (Table 1) reveals that after three successive pumpings of test oil into the CCS cell, both methods give substantially identical results. In virtually all cases the results of the inventive apparatus are within 10% of the D-2602 results, and in the majority of the cases the margin is no greater than approximately 5%. A typical example at $-10°$ C. is plotted in FIG. 7.

In developing the automated CCS, the various control switches of the CCS were hardwired to sequencer 16 as previously explained, the sequencer programmed to perform the steps of FIGS. 5 and 6. With the sequencer in place, the CCS viscosity data of blended motor oils were gathered using both the ASTM D-2602 and the automated methods. In other words, in the laboratory blending plant operating conditions were simulated to see if the automated CCS method provides a good quality control tool for blending various multi-grade motor oils.

In Table 3, the CCS viscosity data are presented for four multi-grade formulated motor oils using the automated CCS procedure. In Table 4, the CCS viscosity data are presented for the same four multi-grade oils. It should also be noted that in Table 3 the sequence of pumping included both going from higher grade to lower grade and from lower grade to higher grade. Upon comparison of the measured CCS viscosities in Tables 3 and 4, it can be seen that after three injections, the automated CCS viscosity numbers again are quite close (within the precision level of ASTM D-2602) to CCS viscosity numbers obtained by using the ASTM D-2062 method.

There has thus been described herein an automated arrangement for providing unattended continuous monitoring viscosity of a product line conveying a particular product, and specifically a petroleum product such as a blended motor oil to improve quality control of a bending process for the product However, both the environment in which the invention is practiced and the parameters for which a sample is tested may differ from the above description without departing from the scope of the invention.

The foregoing description of the preferred embodiment of the invention has been presented for purposes of illustration and description and is not intended to be exhaustive or to limit the invention to the precise forms disclosed, since many modifications and variations are possible in light of the above teaching. The embodiment was chosen and described in order best to explain the principles of the invention and its practical application, thereby to enable others skilled in the art best to utilize the invention in various embodiments and with various modifications as are suited to the particular use contemplated therefor It is intended that the scope of the invention be defined by the claims appended hereto, when interpreted in accordance with full breadth to which they are legally and equitably entitled

APPENDIX

```
0100  REM INITIALIZATION
0200  CS=0
0300  S=0
0400  POKE(-16294)
0500  REM CCS COOLING VALVE OFF, CCS HEATER ON.
0600  POKE(-16296)
0700  REM SAMPLE OIL PUMP OFF
0800  POKE(-16292)
0900  REM CCS MOTOR OFF.
1000  T1=80
1100  T2=200
1200  T3=208
1300  T4=210
1400  T5=240
1500  HOME: PRINT " AUTOMATIC COLD CRANK SIMULATOR ":PRINT : PRINT
1600  POKE 34,2
1700  INPUT "TIME OF DAY(HOUR) = ";TH
1800  INPUT "TIME OF DAY(MINUTE) = ";TM
1900  INPUT "DAY = ";TD
2000  TFF=PEEK(-16285)
2100  POKE(-16295):POKE(-16294): POKE(-16292): REM SAMPLE PUMP ON
2200  J=0
2300  K=0
2400  TMC=0
2500  IF TFF > 125 THEN 3300
2600  I=0
2700  TFF=PEEK(-16285)
2800  I= I+1: IF I > 5000 THEN 6300
2900  IF TFF < 125 THEN 2700
3000  CS=CS+.125
3100  IF CS > T1 THEN 3800
3200  I=0
3300  TFF=PEEK(-16285)
3400  I= I+1: IF I > 5000 THEN 6200
3500  IF TFF > 125 THEN 3300
3600  CS=CS+.125
3700  GOTO 2600
3800  IF CS > T2 THEN 4100
3900  POKE(-16293): POKE(-16296): REM COOLING ON, SAMPLE OFF
4000  GOTO 3200
4100  IF CS > T5 THEN 5500
4200  IF CS > T4 THEN 5000
4300  POKE(-16291): REM CCS MOTOR ON
4400  IF CS < T3 THEN 3200
4500  MC=PDL(1)
4600  TMC=TMC+MC
4700  J=J+1
4800  AMC=TMC/J
4900  GOTO 3200
5000  IF K>0 THEN 3200
5100  PRINT" DAY ";TD;" TIME: ";TH;":";TM;" MOTOR CURRENT: ";AMC
5200  POKE(-16292): POKE(-16294): REM CCS MOTOR OFF, HEATER ON
5300  K=10
5400  GOTO 3200
5500  TM=TM+(CS/60)+S
5600  S=TM−INT(TM)
5700  TH=TH+INT(TM/60)
5800  TD=TD+INT(TH/24)
5900  TH=INT(TH−(24*INT(TH/24)))
6000  TM=INT(TM−(60*INT(TM/60)))
6100  GOTO 2000
6200  PRINT" CLOCK NOT RUNNING"
6300  GOTO 0100
```

TABLE 1

CCS Viscosity Data Using an Automated CCS Method

Temperature $-10°$ C.

| Reference Oil | CL32 | CL38 | CL48 | CL60 | CL32 | CL48 | CL60 | CL38 |
|---|---|---|---|---|---|---|---|---|
|  | 2500 cp | 2900 | 3800 | 5800 | 3800 | 2700 | 4400 | 4800 |
|  | 1950 | 2750 | 4300 | 4000 | 2200 | 4100 | 6600 | 3300 |
|  | 1700 | 2750 | 5300 | 7100 | 1700 | 4350 | 6600 | 3000 |

TABLE 1-continued
CCS Viscosity Data Using an Automated CCS Method

| | 7100 | | | | 3000 | | | |
|---|---|---|---|---|---|---|---|---|

Temperature −15° C.

| Reference Oil | CL25 | CL48 | CL38 | CL32 | CL25 | CL38 | CL48 | CL32 |
|---|---|---|---|---|---|---|---|---|
| 1825 cp | 6200 | 7000 | 4300 | 2400 | 7200 | 6800 | 5100 |
| 1850 | 7800 | 6000 | 5700 | 2000 | 5400 | 7800 | 4100 |
| | 8400 | 5850 | 3550 | 1850 | 5400 | 8000 | 3600 |
| | 8800 | | 3550 | 1800 | | | 3500 |

Temperature −20° C.

| Reference Oil | CL19 | CL14 | CL25 | CL19 | CL14 | CL25 | CL19 | CL14 | CL19 |
|---|---|---|---|---|---|---|---|---|---|
| 1775 cp | 1125 | 3000 | 2250 | 350 | 2900 | 1950 | 960 | 1400 |
| 1750 | 880 | 3350 | 1850 | 800 | 3300 | 1750 | 860 | 1650 |
| | 870 | 3500 | 1750 | 900 | 3500 | 1700 | 840 | 1650 |

| Reference Oil | CL25 | CL14 | CL19 | CL14 | CL25 |
|---|---|---|---|---|---|
| 3000 cp | 1800 | 1850 | 1100 | 2900 |
| 3300 | 1400 | 1770 | 960 | 3350 |
| 3350 | 940 | 1800 | 940 | 3400 |
| | | 1800 | | |

Temperature −25° C.

| Reference Oil | CL14 | CL25 | CL19 | CL25 | CL14 | CL14 | CL19 | CL25 | CL19 | CL14 |
|---|---|---|---|---|---|---|---|---|---|---|
| | 1650 | 6400 | 4500 | 5800 | 3150 | 1600 | 2750 | 7300 | 4650 | 2350 |
| | 1600 | 6900 | 3900 | 6900 | 2350 | 1600 | 3200 | 6600 | 3900 | 1800 |
| | 1600 | 6900 | 3500 | 6900 | 1650 | 1600 | 3300 | 6900 | 3500 | 1650 |
| | | | 3350 | | | | | | | |

TABLE 2
CCS Viscosity Data Using the ASTM D-2602 Method

Temperature −10° C.

| Reference Oil | CL60 | CL38 | CL32 | CL48 |
|---|---|---|---|---|
| | 7100 cp | 2800 | 1800 | 4550 |
| | 7100 | 2800 | 1800 | 4550 |

Temperature −15° C.

| Reference Oil | CL38 | CL32 | CL48 | CL25 |
|---|---|---|---|---|
| | 5850 cp | 3500 | 9200 | 1800 |
| | 5850 | 3500 | 9200 | 1850 |
| | 5700 | | | |

Temperature −20° C.

| Reference Oil | CL14 | CL19 | CL25 |
|---|---|---|---|
| | 900 cp | 1800 | 3500 |
| | 920 | 1800 | 3500 |
| | 900 | | |

Temperature −25° C.

| Reference Oil | CL14 | CL19 | CL25 |
|---|---|---|---|
| | 1650 cp | 3500 | 7300 |
| | 1600 | 3500 | 7300 |

TABLE 3
Cold-Cranking Simulator Viscosity Data of Multi-Grade Motor Oils* using an Automated CCS Procedure
CCS Viscosity (cp)

| 20W-50 | 15W-40 | 10W-40 | 5W-30 | 10W-40 | 15W-40 |
|---|---|---|---|---|---|
| 3000 cp | 3800 cp | 3800 cp | 3550 cp | 2300 cp | 2550 cp |
| 3400 | 3100 | 3400 | 3300 | 2800 | 2850 |
| 3400 | 3000 | 3175 | 3175 | 2925 | 2850 |
| | 2950 | 3175 | 3175 | 2975 | 2875 |

| 20W-50 | 5W-30 | 15W-40 | 5W-30 | 20W-50 | 10W-40 | 20W-50 |
|---|---|---|---|---|---|---|
| 2700 cp | 4900 cp | 2850 cp | 4100 cp | 1725 cp | 3650 C | 2050 cp |
| 3200 | 3400 | 2950 | 3400 | 2600 | 3350 | 2900 |
| 3400 | 3350 | 2850 | 3300 | 3200 | 3200 | 3250 |
| 3400 | 3300 | 2875 | 3200 | 3300 | 3175 | 3400 |

TABLE 4
Cold-Cranking Simulator Viscosity Data of Multi-Grade Motor Oils* using ASTM D-2602 Procedure
CCS Viscosity (cp)

| 5W-30 | 10W-40 | 15W-40 | 20W-40 |
|---|---|---|---|
| 3175 | 3050 | 2850 | 3450 |
| 3100 | 3100 | 2850 | 3450 |

*The oils in Tables 3 and 4 are as follows:

| Sample Used | Test Temperature |
|---|---|
| Pennzoil multivis HD SAE 5W-30 | −25° C. |
| Pennzoil multivis HD SAE 10W-40 | −20° C. |
| Pennzoil long life SAE 15W-40 | −15° C. |
| Pennzoil GT performance SAE 20W-50 | −10° C. |

What is claimed is:

1. In a cold cranking simulator for multi-viscosity motor oils, including therein a controllable cooling and heating apparatus for controlling temperature of a sample delivered thereto and a motor, the improvement comprising means for integrating said cold cranking simulator into a plant control system to provide a substantially continuous and autonomous monitoring of viscosity of motor oil flowing in a conduit, thereby eliminating a requirement for manual intervention in the monitoring process, including:

single sample providing means including means for retrieving a discrete sample from the conduit and means for introduction of the sample into a measurement chamber of said cold cranking simulator sequencing means for controlling said single sample providing means and said cold cranking simulator to provide substantially continuous and unattended withdrawal and delivery of samples from the conduit and to said cold cranking simulator, respectively; and further comprising auxiliary pump means responsive to timing and control signals provided by said sequencing means for providing samples to said cold cranking simulator measuring chamber when pressure in said conduit is below a predetermined threshold value.

2. An improved cold cranking simulator as recited in claim 1 wherein said sequencing means further causes said single sample providing means to deliver said samples to the measuring chamber only at times when the chamber is being heated for displacing heated, low viscosity, remnants of a previous sample by a cooler, higher viscosity, sample used as a piston to displace the previous sample to effect cleaning of the measuring chamber and to obviate a separate operation of cleansing of, and application of a solvent to, the chamber.

3. An improved cold cranking simulator as recited in claim 2 wherein:
said single sample providing means comprises controllable pump means connected between the conduit for the motor oil and the measuring chamber for controllably pumping samples from the conduit to the measuring chamber responsively to said sequencing means, and
said sequencing means comprises programmable microprocessor means programmed for operating said pump means when the measuring chamber is being heated.

4. An improved cold cranking simulator as recited in claim 2 wherein:
said single sample providing means comprises a controllable solenoid valve means connected between the conduit for the motor oil and the measuring chamber for controllably delivering samples from the conduit to the measuring chamber responsively to said sequencing means, and
said sequencing means comprises programmable microprocessor means programmed for operating said solenoid valve means when the measuring chamber is being heated.

5. An improved cold cranking simulator as recited in claim 1 wherein said sequencing means comprises programmable processor means programmed for operating said single sample providing means,
said programmable processor means operable responsive to current drawn by a motor of said cold cranking simulator to provide control signals for controlling operation of said cold cranking simulator.

6. An improved cold cranking simulator as recited in claim 5, said sequencing means further comprising means for converting magnitude of current drawn by the motor of said cold cranking simulator to a time duration and for outputting said control signals at times determined by said time duration.

7. In a cold cranking simulator for multi-viscosity motor oils, including therein a controllable cooling and heating apparatus for controlling temperature of a sample delivered thereto and a motor, the improvement comprising
means for integrating said cold cranking simulator into a plant control system to provide a substantially continuous and autonomous monitoring of viscosity of motor oil flowing in a conduit, thereby eliminating a requirement for manual intervention in the monitoring process, including:
sample providing means operable for repeatedly retrieving a sample from the conduit and for introduction of the sample into a measurement chamber of said cold cranking simulator, and
sequencing means for controlling said sample providing means and said cold cranking simulator to provide substantially continuous and unattended withdrawal and delivery of samples from the conduit and to said cold cranking simulator, respectively,
said sequencing means comprising programmable processor means programmed to operate responsively to current drawn by a motor of said cold cranking simulator to provide control signals for controlling operation of said sample providing means and said cold cranking simulator,
said sequencing means further comprising current converting means for converting magnitude of current drawn by the motor of said cold cranking simulator to a time duration and for outputting said control signals at times determined by said time duration.

8. An improved cold cranking simulator as recited in claim 7 wherein said processor means is programmed to cause a sequence of operations to be performed, said sequence including the steps of:
operating said controllable cooling and heating apparatus to warm the measurement chamber of said cold cranking simulator,
thereafter, activating said sample providing means to provide to the measurement chamber of said cold cranking simulator a sample of said motor oil flowing in the conduit;
thereafter, cooling the measurement chamber;
terminating activation of said sample providing means; and
starting operation of the motor of said cold cranking simulator.

9. An improved cold cranking simulator as recited in claim 8 wherein said processor means is further programmed to cause performance of a further sequence of operations including the further steps of:
storing a value of current drawn by the motor of said cold cranking simulator;
thereafter, stopping operation of the motor of said cold cranking simulator; and
terminating the cooling of the measurement chamber.

10. An improved cold cranking simulator as recited in claim 9 wherein said processor means is further programmed to compute an average value of the current drawn by the motor of said cold cranking simulator and to output to a user an indication of time and of the average current, thus providing an output indication of viscosity of said sample of motor oil.

11. An improved cranking simulator as recited in claim 7 wherein said cold cranking simulator includes a control panel having a plurality of control switches and wherein said control switches are hardwired to said sequencing means for receiving directly said control signals therefrom.

12. In a cold cranking simulator for multi-viscosity motor oils, including therein a controllable cooing and heating apparatus for controlling temperature of a sample delivered thereto and a motor, the improvement comprising
means for integrating said cold cranking simulator into a plant control system to provide a substantially continuous and autonomous monitoring of viscosity of motor oil flowing in a conduit, thereby eliminating a requirement for manual intervention in the monitoring process, including:

single sample providing means including means for retrieving a discrete sample from the conduit and means for introduction of the sample into a measurement chamber of said cold cranking simulator, sequencing means for controlling said single sample providing means and said cold cranking simulator to provide substantially continuous and unattended withdrawal and delivery of samples from the conduit and to said cold cranking simulator, respectively;

wherein said sequencing means comprises programmable processor means programmed for operating said single sample providing means, said programmable processor means operable responsive to current drawn by a motor of said cold cranking simulator to provide control signals for controlling operation of said cold cranking simulator, and said sequencing means further comprising means for converting magnitude of current drawn by the motor of said cold cranking simulator to a time duration and for outputting said control signals at times determined by said time duration.

* * * * *